US007127757B2

(12) United States Patent
Roberto

(10) Patent No.: US 7,127,757 B2
(45) Date of Patent: Oct. 31, 2006

(54) ADJUSTABLE TRACTION TABLE

(76) Inventor: Christopher Matthew Roberto, 11 Memory La., Bloomingburg, NY (US) 12721

( * ) Notice: Subject to any disclaimer, the term of this patent is extended or adjusted under 35 U.S.C. 154(b) by 319 days.

(21) Appl. No.: 10/795,014

(22) Filed: Mar. 5, 2004

(65) Prior Publication Data

US 2005/0197670 A1 Sep. 8, 2005

(51) Int. Cl.
*A61F 5/00* (2006.01)

(52) U.S. Cl. .......................... 5/613; 606/242; 606/243; 606/245

(58) Field of Classification Search .................... 5/613, 5/616; 601/24, 26; 606/242–245, 237, 240
See application file for complete search history.

(56) References Cited

U.S. PATENT DOCUMENTS 2,702,733 A * 2/1955 Lorang ....................... 606/242
3,226,106 A * 12/1965 Johnson et al. ................ 5/613
3,998,218 A * 12/1976 Lane et al. ................. 606/242
4,726,358 A * 2/1988 Brady ......................... 606/243
5,060,636 A * 10/1991 Bell ........................... 606/243
6,681,770 B1 * 1/2004 Dreher ....................... 128/845

* cited by examiner

*Primary Examiner*—Michael Trettel
(74) *Attorney, Agent, or Firm*—Sanford J. Asman

(57) ABSTRACT

The adjustable traction table has a pair of patient supports, one of which is longer than the other. The patient supports are mounted to a base having a fixed portion and a sliding portion. A pair of screw jacks attaches each of the patient supports to the fixed portion of the base, and to the sliding portion of the base, thereby allowing the height of each end of each of the patient supports to be independently adjusted whereby each of the patient supports can slope upward toward the end away from the other patient support, downward toward the end away from the other patient support, or relatively horizontal. Further, a screw jack which is horizontally mounted between the fixed portion of the base and the sliding portion of the base provides an adjustment means which is able to provide an adjustable horizontal separation between the patient supports.

10 Claims, 6 Drawing Sheets

ADJUSTABLE TRACTION TABLE

BACKGROUND OF THE INVENTION

The present invention relates to apparatus for use in treating patients. In particular, the invention relates to an adjustable traction table of the type used by chiropractors in the treatment of a patient's back and spine.

The treatment of patients by chiropractors often involves procedures used to assist in the alignment of a patient's back and spine in order to correct abnormalities and alleviate or diminish pain.

Various types of apparatus, particularly tables, such as traction tables, have been used by chiropractors to assist in the treatment of their patients. A common problem with the various types of apparatus heretofore available has been that they could only be used in a particular type of procedure due to limitations in configuration.

SUMMARY OF THE INVENTION

In accordance with the present invention, an adjustable traction table has been developed in which the traction table includes a pair of patient supports. In the preferred embodiment of the invention, one of the patient supports is longer than the other support. The supports are each attached to a base using at least a pair of vertically adjustable means, with one of the supports, preferably the shorter one, being attached to a sliding portion of the base, whereby the patient supports can be moved toward, or away from, each other. In the preferred embodiment of the invention, all aspects of vertical and horizontal movement of the patient supports relative to one another is positively controlled by using scissor jacks. A further advantage provided by the use of the scissor jacks is that the supports can be adjusted even when a very heavy patient is on the table.

DETAILED DESCRIPTION OF AN EXEMPLARY EMBODIMENT

Figure 1:
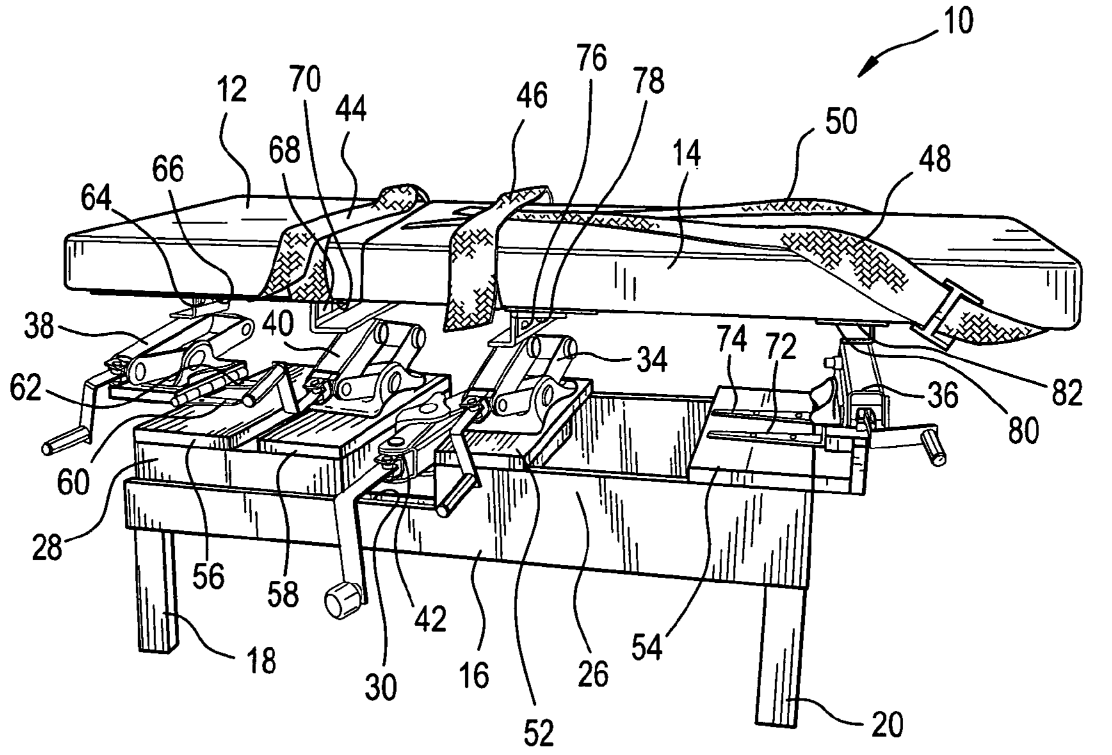
FIG. 1 is a perspective view of the adjustable traction table of the present invention with the patient supports in their lowest positions, and with their respective interior portions adjacent to one another.

Referring to FIG. 1, in accordance with the present invention, an adjustable traction table 10, intended for use in chiropractic procedures, is shown. The table 10 includes a pair of patient supports 12, 14 on which a patient (not shown) can be placed for treatment of his back or spine. As shown, the patient support 12 is somewhat shorter than the patient support 14. The table 10 is further comprised of a base 16, which supports the patient supports 12, 14 in a manner which provides for a variety of adjustments of the relative positions of the patient holding surfaces, as will be explained hereinafter.

The base 16 is substantially rectangular when viewed from above, and it is displaced from the floor by legs 18, 20 (shown), and 22, 24 (not visible in FIG. 1). The base 16 has a fixed portion 26, and a sliding portion 28. The sliding portion 28 is slidably affixed to a pair of tracks 30 (visible), and 32 (not visible in FIG. 1) on the base 16.

With continued reference to FIG. 1, in accordance with the preferred embodiment of the invention, a pair of vertically extendable means, comprising, in the preferred embodiment of the invention, a pair of scissor jacks 34, 36 are mounted to the fixed portion 26 of the base 16. The scissor jacks 34, 36 are also attached to the underside of the longer patient support 14. Similarly, a second pair of vertically extendable means, also comprising, in the preferred embodiment of the invention, a pair of scissor jacks 38, 40 are mounted to the sliding portion 28 of the base 16. The scissor jacks 38, 40 are also attached to the underside of the shorter patient support 12. Finally, there is a horizontally extendable means, also comprising a scissor jack 42, in the preferred embodiment of the invention, which is used to horizontally displace the sliding portion 28 of the base 16 from the fixed portion 26 of the base 16. In the preferred embodiment of the invention, all of the scissor jacks 34, 36, 38, 40, 42, are Item No. HS-S2 scissor jacks, available from Mastercraft Tools Florida, Inc. 1354 NW 78$^{th}$ Avenue, Miami, Fla. 33126, as Article No. HJ-S2.

The patient supports 12, 14 each include a relatively firm material, such as a urethane foam, covered by a suitable material, such as vinyl. Finally, the patient supports 12, 14 include straps 44, 46, 48, 50, which may be used to assist in maintaining a patient in a particular position on the patient supports 12, 14.

As will be recognized by those skilled in the art, while the vertically adjustable means 34, 36, 38, 40, and the horizontally adjustable means 42, are all scissor jacks in the preferred embodiment of the invention, they may be replaced by other mechanisms which perform the same, or substantially the same functions without departing from the present invention. Thus, one or more of the scissor jacks could be replaced by hydraulic lifting means. Alternatively, the scissor jacks shown, which are operated by hand cranks, could be replaced by electrically operated lifts, in which case the extension of each could be controlled by either a switch or by an electronic controller or by a computer. Similarly, the horizontally adjustable means 42, could be replaced by hydraulic apparatus, and/or it could include an electrically operated means. By way of example, motorized lifts, which can be used either horizontally or vertically and which use a rack and pinion apparatus are manufactured and sold by Auton Motorized Systems, 28220 Avenue Crocker, Suite 405, Valencia, Calif. 91355 (http://www.auton.com).

As set forth above, the sliding portion 28 of the base 16 is mounted on tracks 30, 32. In the preferred embodiment of the invention, the tracks are comprised of "Classic Wood Center Mount Drawer Slides", Part No. 24877, available from http://www.rockler.com, although other sliding hardware could be used.

With continued reference to FIG. 1, in the preferred embodiment of the invention, the base 16 is constructed of three-quarter inch thick oak. The base 16 has an overall length of about 40 inches, and a width of about 17.5 inches. The legs 18, 20, 22, 24 hold the base 16 about 8 inches off the floor. The fixed portion 26 of the base 16 has an apron which is about 4½ inches high, while the apron portion of the base 16 under the sliding portion 28 is about 2 inches high, so that when the sliding portion 28 is mounted thereon, the top of the sliding portion 28 and the top of the fixed portion 26 are substantially the same.

In order to mount the jacks 34, 36 on the fixed portion 26 of the base 16, a pair of horizontal supports 52, 54 are mounted to the upper portion of the fixed portion 26 of the base. Similarly, another pair of horizontal supports 56, 58, which support the jacks 38, 40, are mounted to the upper portion of the sliding portion 28 of the base 16. Finally, the horizontally mounted jack 42 is mounted between the fixed portion 26 and the sliding portion 28 of the base.

In order to allow the short patient support 12 to be raised at an angle to the horizontal, the jack 38 is affixed to the horizontal support 56 using a pair of hinges 60, 62, which allow the jack 38 to tilt. The jack 40 is mounted directly to the horizontal support 58. The tops of the vertical jacks 38, 40 are each affixed to the bottom of the short patient support 12 by pairs of hinges 64, 66 and 68, 70, respectively. Similarly, to allow the long patient support 14 to raise and tilt, in the preferred embodiment of the invention the jack 34 is mounted directly to the horizontal support 52, while the jack 36 is mounted to the horizontal support 54 using a pair of hinges 72, 74. The tops of the jacks 34, 36 are each affixed to the bottom of the long patient support 14 by pairs of hinges 76, 78 and 80, 82, respectively.

Based upon the foregoing configuration of parts, the adjustable traction table 10 of the present invention provides an apparatus which can be adjusted to meet virtually any desired configuration. As the scissor jacks provide a very large mechanical advantage, the patient supports 12, 14 can be easily adjusted vertically and horizontally relative to one another, even if a heavy patient is on the table 10.

Figure 2:
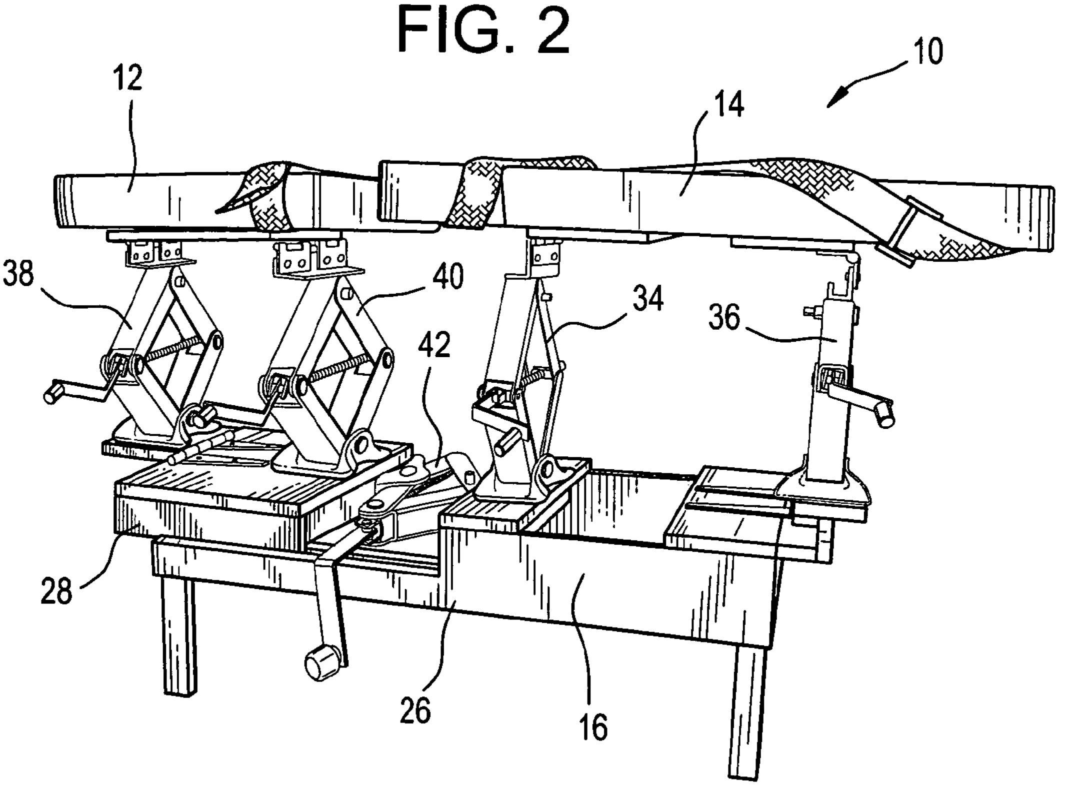
FIG. 2 is a perspective view of the adjustable traction table of the present invention with the patient supports in their highest positions, and with their respective interior portions adjacent to one another.

By way of example, with reference to FIG. 2, the table 10 can be adjusted so that the patient supports 12, 14 are quite high, relative to the base 16. This is accomplished by cranking the jacks 34, 36, 38, 40, in order to extend them up, vertically. Also, as shown in FIG. 2, the jack 42 may be partially extended in order to separate the shorter patient support 12 from the longer patient support 14, as that causes the sliding portion 28 of the base 16 to move away from the fixed portion 26.

Figure 3:
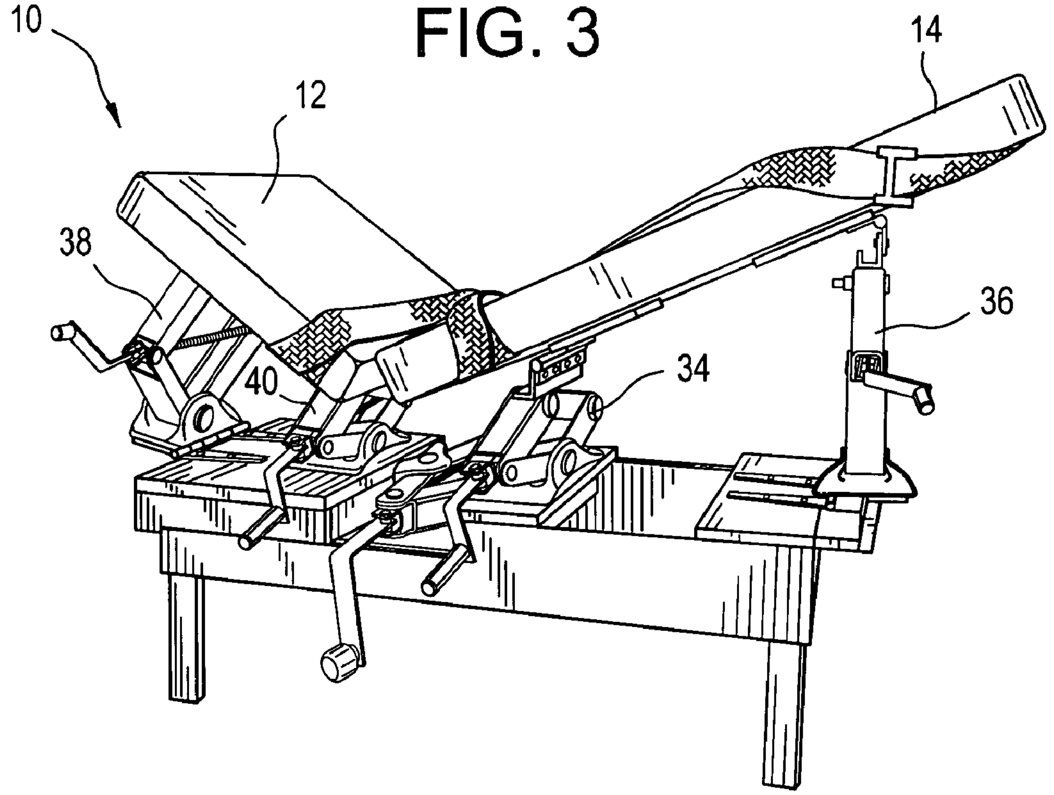
FIG. 3 is a perspective view of the adjustable traction table of the present invention with their patient supports adjacent to one another and adjusted such that they each slope upward from their respective interior edges, thereby resulting in them having their end portions higher than their central portions.

With reference to FIG. 3, by adjusting the jacks 34, 36, 38, 40 so that jacks 34 and 40 are not extended as much as jacks 36 and 38, the patient support surfaces 12, 14 will slope upward on their outer portions, and their inner portions can be brought adjacent to one another by using jack 42 to bring the sliding portion 28 of the base 16 closer to the fixed portion 26 of the base.

Figure 4:
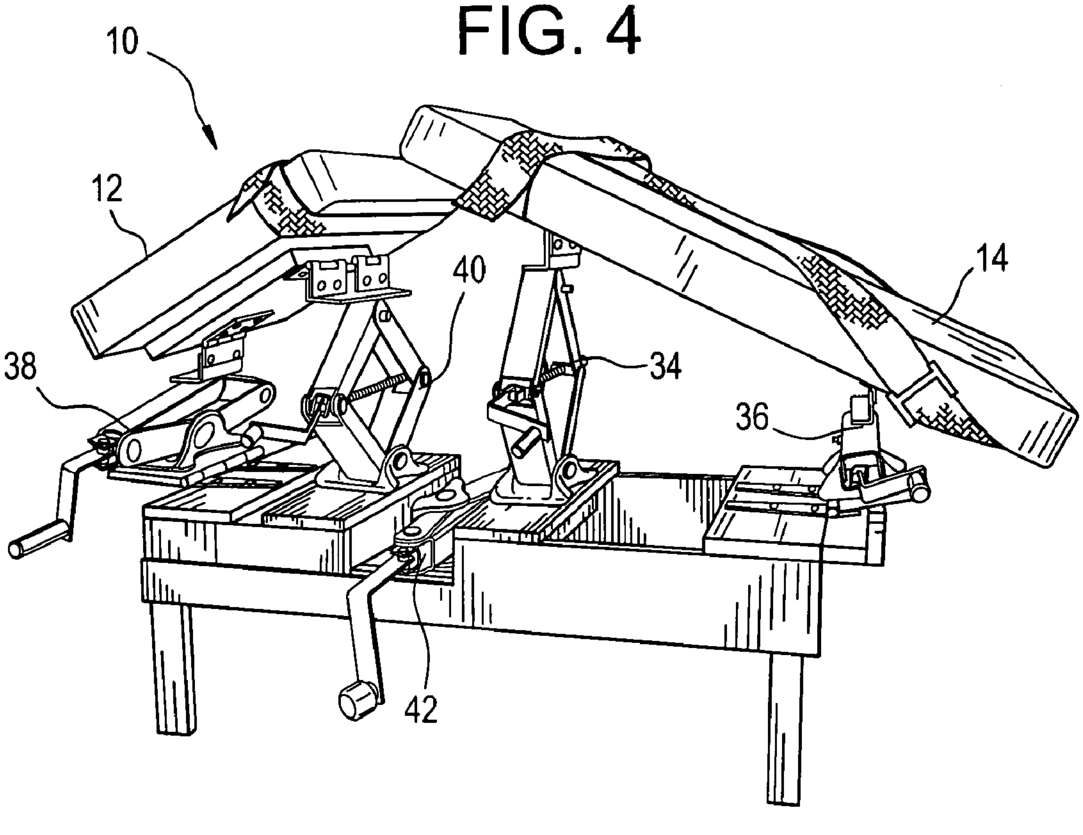
FIG. 4 is a perspective view of the adjustable traction table of the present invention with the patient supports adjusted so that they are somewhat spaced from one another, and such that they each slope downward from their respective interior edges.

With reference to FIG. 4, the opposite result, i.e., having the patient support surfaces 12, 14 somewhat spaced from one another, and having them each slope downward from their respective interior edges is accomplished by extending the interior jacks 34, 40 more than the exterior jacks 36, 38. The patient supports 12, 14 are separated by extending horizontal jack 42 somewhat in order to move the sliding portion 28 of the base 16 away from the fixed portion 26.

Figure 5:
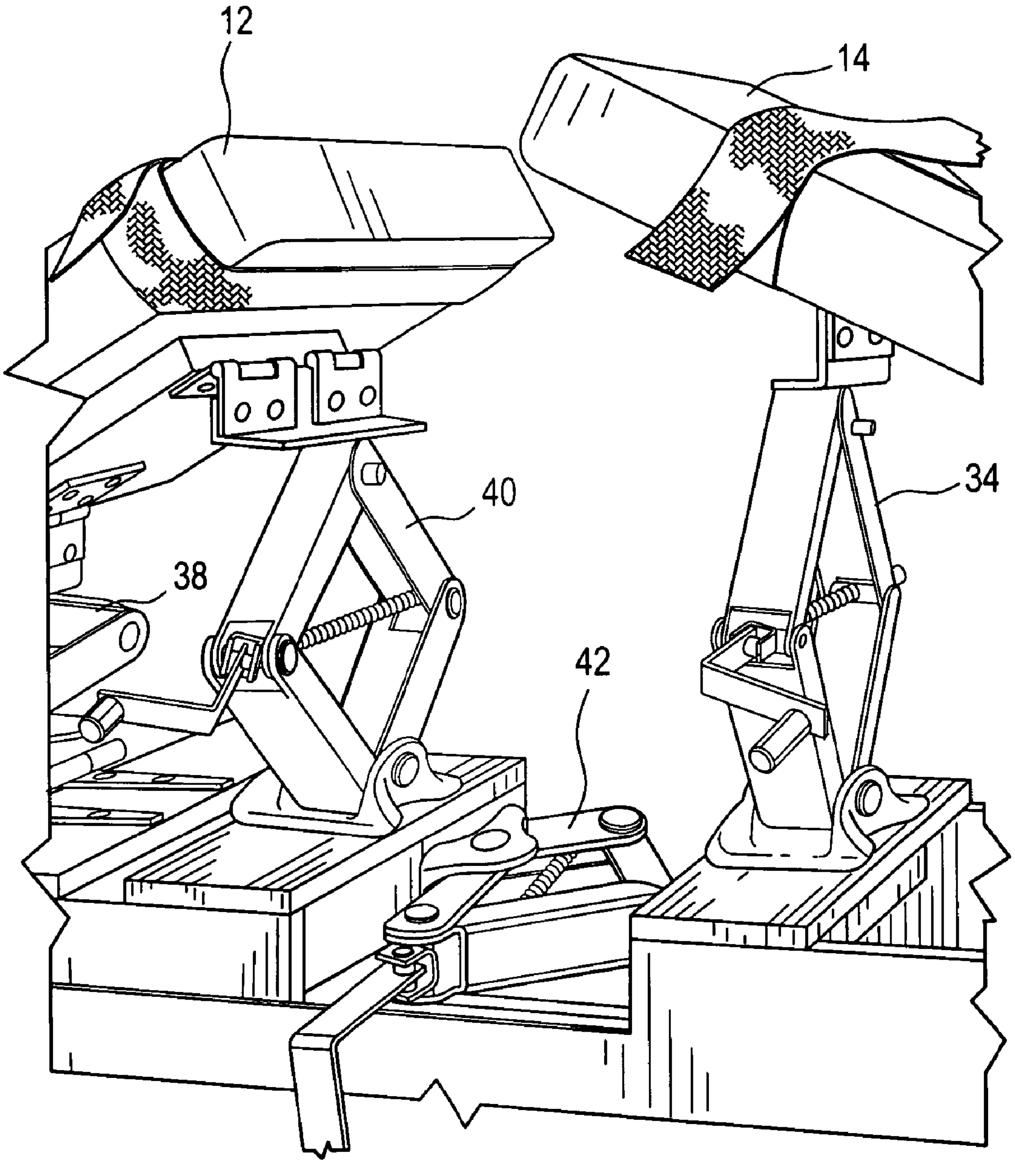
FIG. 5 is a close-up perspective view of the adjustable traction table of the present invention with the patient supports adjusted so that they are more spaced from one another than they are in FIG. 4, and such that they each slope downward from their respective interior edges.

With reference to FIG. 5, the patient support surfaces 12, 14 can be further adjusted to provide additional space between them by further extending horizontal jack 42.

Figure 6:
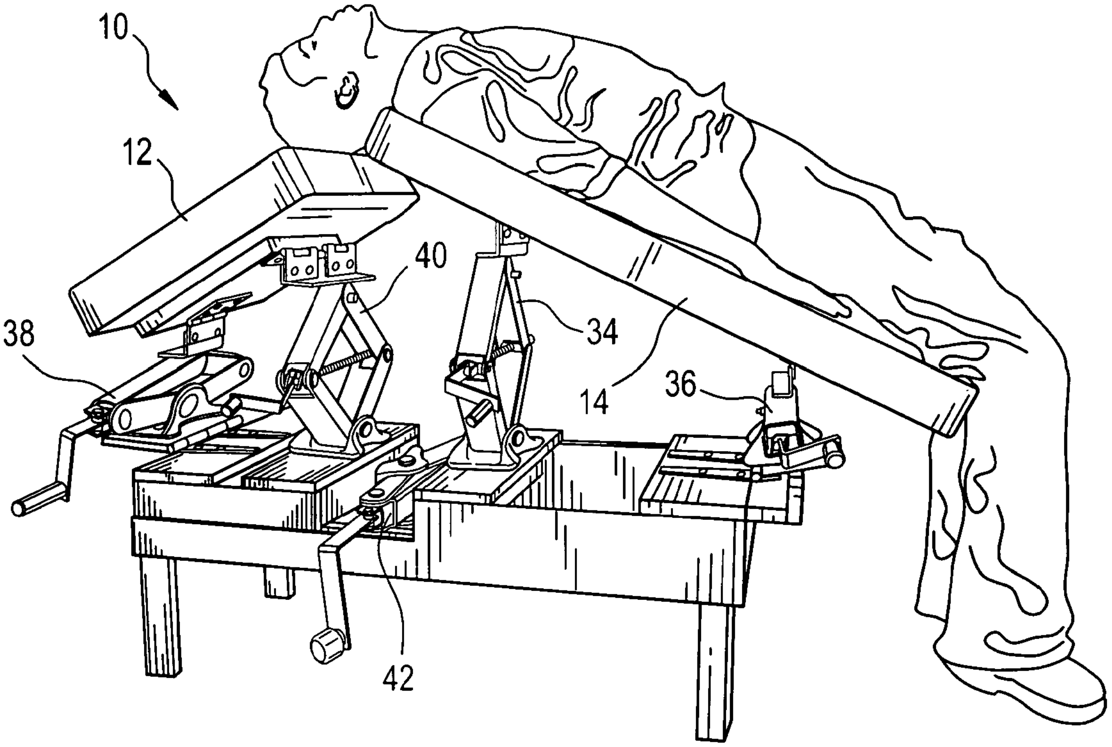
FIG. 6 is a side view of the adjustable traction table of the present invention with the patient supports adjusted so that they are highest at their respective interior edges, showing a patient on the longer of the support surfaces.

FIG. 6 illustrates one manner of using the adjustable traction table 10 in which the longer patient support surface 14 is adjusted to slope upward from the end whereby a patient can have his thighs and back on the support surface 14, with his lower legs extending downward toward the floor.

Figure 7:
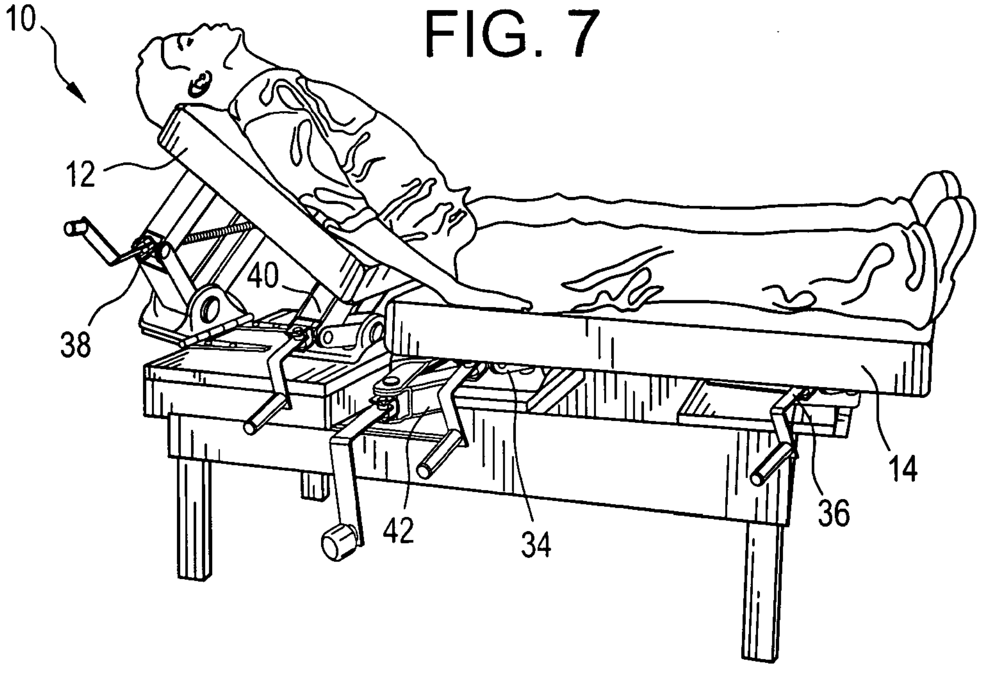
FIG. 7 is a side view of the adjustable traction table of the present invention with the patient supports adjusted so that they each slope upward from their respective interior edges, with the longer patient support sloping far less than the shorter patient support, showing a patient lying across both of the support surfaces.

FIG. 7 illustrates another manner of using the adjustable traction table 10 in which the longer patient support surface 14 is adjusted so that it slopes upward slightly toward its outside end, while the short patient support surface 12 slopes further upward, whereby a patient lying on the table 10 has his legs supported by the lower patient support surface, while his back is supported by the short patient support surface 12, with the patient's torso sloping upward toward the outside end of the short patient support surface 12.

Figure 8:
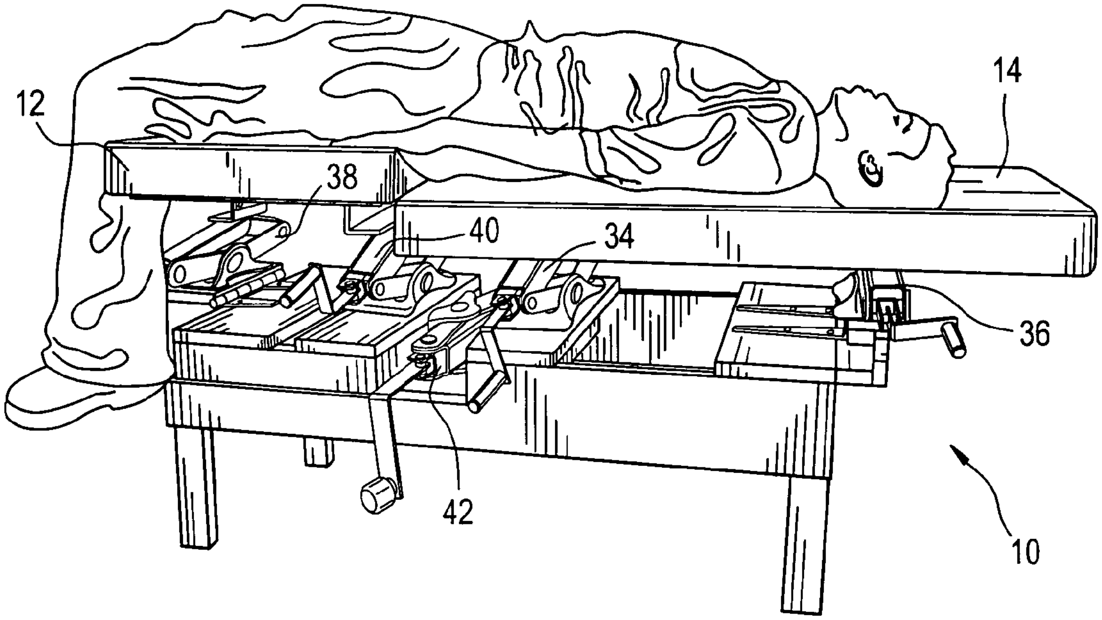
FIG. 8 is a side view of the adjustable traction table of the present invention with the patient supports being adjusted so that they are each substantially horizontal, with the shorter support surface being higher than the longer support surface, with a patient lying across both of the support surfaces.
Figure 9:
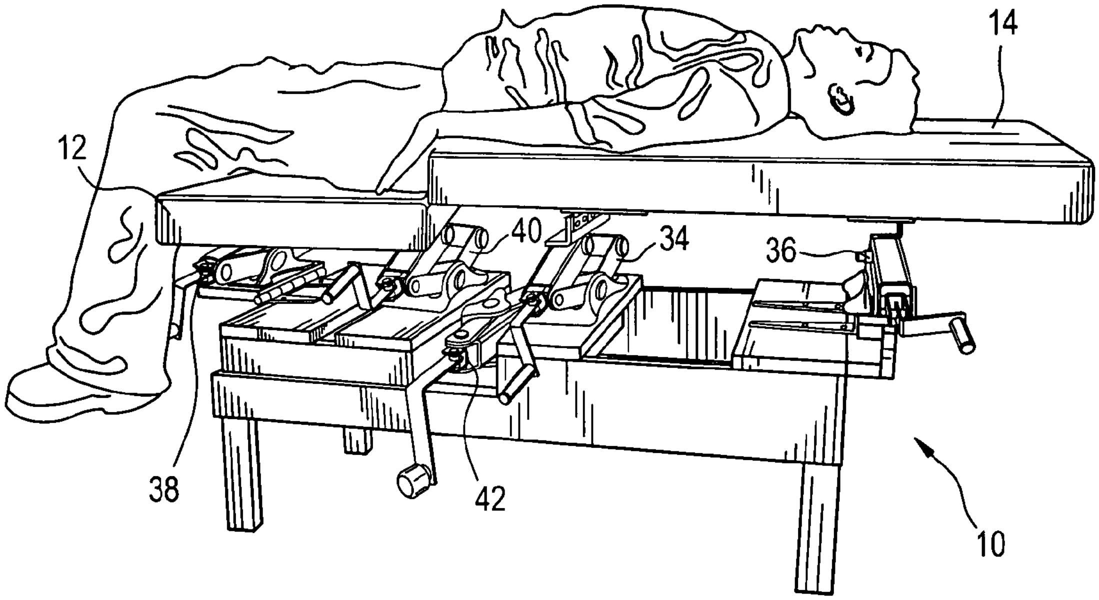
FIG. 9 is a side view of the adjustable traction table of the present invention with the patient supports being adjusted so that they are each substantially horizontal, with the shorter support surface being lower than the longer support surface, with a patient lying across both of the support surfaces.

FIGS. 8 and 9 each illustrate a patient having his thighs supported by the short patient support 12, his back and head supported on the long patient support 14, and his lower legs extending down. In each case the patient supports 12, 14 are substantially horizontal, and they are relatively close to one another. However, in the configuration of FIG. 8 the short patient support 12 is vertically higher than the long patient support 14, whereas in the configuration of FIG. 9 the short patient support 12 is vertically lower than the long patient support 14.

Figure 10:
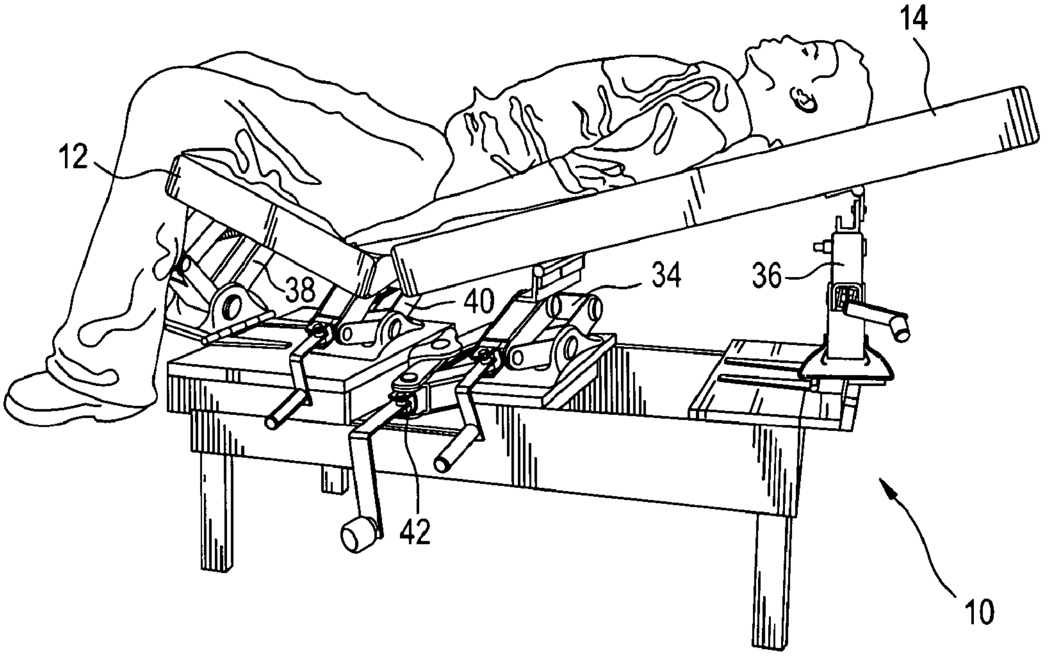
FIG. 10 is a side view of the adjustable traction table of the present invention with the patient supports being adjusted so that they each slope upward from their interior edge, with a patient lying across both of the support surfaces.
Figure 11:
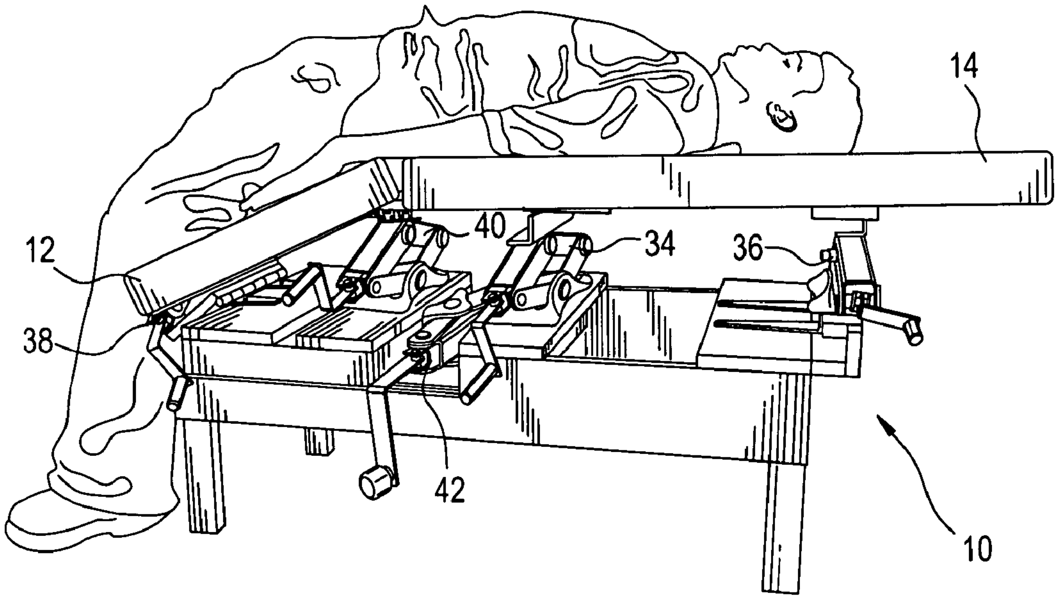
FIG. 11 is a side view of the adjustable traction table of the present invention with the patient supports being adjusted so that they each slope downward from their interior edge, with a patient lying across both of the support surfaces.

FIGS. 10 and 11 also each illustrate a patient having his thighs supported by the short patient support 12, his back and head supported on the long patient support 14, and his lower legs extending down, as in FIGS. 8 and 9. However, in the configuration of FIG. 10, the patient supports 12, 14 each slope upward as they extend away from the middle of the table 10, whereas in the configuration of FIG. 11, the short patient support 12 slopes downward, while the long patient support 14 is relatively horizontal.

In the configurations of the table 10 illustrated in FIGS. 8–11, the same portions of the patient contact the same portions of the table 10, i.e., the patient's back and head are on the long support 14, with his thighs are on the short support 12, with his knees bent over the end of the short support 12. As will be obvious to those skilled in the art, the adjustable tension table 10 of the present invention provides an apparatus which can be adjusted to realign the patient's head, back, hips, and legs, all without changing the position of the patient on the table 10.

Due to the differences in the lengths of the patient supports 12, 14, the ability to slope either of the supports 12, 14 in any desired manner, and the ability to move the supports 12, 14 toward or away from each other, the table 10 also provides a single apparatus which can be used in a variety of procedures, all of which is further assisted by the infinitely variable height adjustments made possible by the vertical jacks 34, 36, 38, 40, combined with the lateral movement provided by horizontal jack 42.

The foregoing features are further enhanced by the hinges used to attach the tops of the vertical jacks 34, 36 and 38, 40 to the undersides of the patient supports 14, 12, respectively. Further, when the outer jack 36, which is attached to the long patient support 14, or the outer jack 38 which is attached to the short patient support 12 is extended more than the inner jacks 34, 40, the hinges used to mount the outer jacks 36, 38 to the fixed portion 26 and sliding portion 28 of the base 16, respectively, allow the outer jacks 36, 38 to pivot inward, rather than stress their respective mounting points.

Those skilled in the art will understand that numerous variations, some of which have been discussed herein, can be made without departing from the spirit or scope of the present invention.

I claim:

1. An adjustable traction table for use in chiropractic procedures, comprising:

(a) a base, said base having a fixed portion and a sliding portion, said sliding portion being axially moveable relative to said fixed portion, said fixed portion of said base having a central portion and an end, said sliding portion of said base having a central portion and an end, said central portion of said fixed portion of said base being adjacent to said central portion of said sliding portion of said base, said end portion of said fixed portion of said base being remote from said central portion of said sliding portion of said base, and said end of said sliding portion of said base being remote from said central portion of said fixed portion of said base;

(b) a first pair of vertical adjustment means mounted on said fixed portion of said base, one of said first pair of vertical adjustment means being mounted in the central portion of the fixed portion of said base, and the other one of said first pair of vertical adjustment means being mounted substantially at the end of said fixed portion of said base;

(c) a first patient support affixed to the top of said first pair of vertical adjustment means;

(d) a second pair of vertical adjustment means mounted on said sliding portion of said base, one of said second pair of vertical adjustment means being mounted in the central portion of said sliding portion of said base, and the other one of said second pair of vertical adjustment means being mounted substantially at the end of said sliding portion of said base;

(e) a second patient support affixed to the top of said second pair of vertical adjustment means;

(f) at least one horizontal adjustment means mounted between, and connecting, said fixed portion of said base and said sliding portion of said base, whereby either of said first patient support and said second patient support can be independently configured to have any desired slope and height relative to said base, and said first patient support and said second patient support can be configured to have any desired horizontal spacing relative to each other.

2. The adjustable traction table of claim 1 in which the tops of said first pair of vertical support means are attached to the bottom of said first patient support using hinge means, whereby stress at their respective attachments is reduced when said first pair of vertical adjustment means are adjusted such that they are not at the same height, thereby facilitating the sloping of said first patient support.

3. The adjustable traction table of claim 2 in which the bottom of the outer one of said first pair of vertical support means is attached to said fixed portion of said base using hinge means, whereby stress at its bottom attachment is reduced when said outer one of said first pair of vertical adjustment means is adjusted such that it is higher than the inner one of said first pair of vertical adjustment means, thereby allowing the top of said outer vertical adjustment means to slope toward the top of said inner vertical adjustment means, facilitating the sloping of said first patient support, such that it is higher at the end than it is in the middle without adding additional stress to the lower attachment point of said outer vertical adjustment means of said first pair.

4. The adjustable traction table of claim 1 in which the tops of said second pair of vertical support means are attached to the bottom of said second patient support using hinge means, whereby stress at their respective attachments is reduced when said second pair of vertical adjustment means are adjusted such that they are not at the same height, thereby facilitating the sloping of said second patient support.

5. The adjustable traction table of claim 4 in which the bottom of the outer one of said second pair of vertical support means is attached to said sliding portion of said base using hinge means, whereby stress at its bottom attachment is reduced when said outer one of said second pair of vertical adjustment means is adjusted such that it is higher than the inner one of said second pair of vertical adjustment means, thereby allowing the top of said outer vertical adjustment means to slope toward the top of said inner vertical adjustment means, facilitating the sloping of said second patient support, such that it is higher at the end than it is in the middle without adding additional stress to the lower attachment point of said outer vertical adjustment means of said second pair.

6. The adjustable traction table of claim 1 in which said first patient support is longer than said second patient support.

7. The adjustable traction table of claim 1 in which said vertical adjustment means are comprised of jacks.

8. The adjustable traction table of claim 7 in which said jacks are scissor jacks.

9. The adjustable traction table of claim 1 in which said horizontal adjustment means is comprised of a jack.

10. The adjustable traction table of claim 9 in which said jack is a scissor jack.

* * * * *